(12) United States Patent
Hsieh et al.

(10) Patent No.: US 11,455,498 B2
(45) Date of Patent: Sep. 27, 2022

(54) MODEL TRAINING METHOD AND ELECTRONIC DEVICE

(71) Applicants: Acer Incorporated, New Taipei (TW); National Yang-Ming University, Taipei (TW)

(72) Inventors: Cheng-Tien Hsieh, New Taipei (TW); Chun-Hsien Yu, New Taipei (TW); Shih-Ho Huang, New Taipei (TW); Meng-Che Cheng, New Taipei (TW); Kun-Hsien Chou, Taipei (TW); Ching-Po Lin, Taipei (TW); Liang-Kung Chen, Taipei (TW)

(73) Assignees: Acer Incorporated, New Taipei (TW); National Yang-Ming University, Taipei (TW)

( * ) Notice: Subject to any disclaimer, the term of this patent is extended or adjusted under 35 U.S.C. 154(b) by 284 days.

(21) Appl. No.: 16/831,821

(22) Filed: Mar. 27, 2020

(65) Prior Publication Data
US 2021/0216826 A1 Jul. 15, 2021

(30) Foreign Application Priority Data
Jan. 10, 2020 (TW) ................. 109100915

(51) Int. Cl.
*A61B 5/00* (2006.01)
*A61B 5/055* (2006.01)
(Continued)

(52) U.S. Cl.
CPC .......... *G06K 9/6262* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 11,260,248 B2 * 3/2022 Khuri-Yakub ......... G16H 20/40
2016/0239969 A1 * 8/2016 Davatzikos .......... G06K 9/6247
(Continued)

FOREIGN PATENT DOCUMENTS

CN 105046709 11/2015
CN 106971410 7/2017
(Continued)

OTHER PUBLICATIONS

Wikipedia, "Training, validation, and test sets," Dec. 14, 2019, pp. 1-5. Available at: https://en.wikipedia.org/w/index.php?title=Training,_validation,_and_test_sets&oldid=930696087.
"Search Report of Europe Counterpart Application", dated Oct. 9, 2020, p. 1-p. 11.

*Primary Examiner* — Soo Shin
(74) *Attorney, Agent, or Firm* — JCIPRNET (57) ABSTRACT

A model training method and an electronic device are provided. The method includes the following steps: establishing a brain age prediction model according to a training set; adjusting a parameter in the brain age prediction model according to a validation set; inputting a test set into the brain age prediction model with the adjusted parameter to obtain a plurality of first predicted brain ages; determining whether the first predicted brain ages satisfy a first specific condition; and completing training of the brain age prediction model when the first predicted brain ages satisfy the first specific condition.

9 Claims, 6 Drawing Sheets

(51) Int. Cl.
    *G06K 9/62*      (2022.01)
    *G06N 20/00*      (2019.01)
    *G06N 5/04*      (2006.01)
    *G06T 7/00*      (2017.01)
    *G16H 30/40*      (2018.01)
    *G16H 50/20*      (2018.01)
    *G16H 50/30*      (2018.01)
    *G16H 50/50*      (2018.01)

(52) U.S. Cl.
    CPC .......... *A61B 5/7267* (2013.01); *G06K 9/6256* (2013.01); *G06N 5/04* (2013.01); *G06N 20/00* (2019.01); *G06T 7/0014* (2013.01); *G16H 30/40* (2018.01); *G16H 50/20* (2018.01); *G16H 50/30* (2018.01); *G06T 2207/20081* (2013.01); *G06T 2207/30016* (2013.01)

(56) References Cited

U.S. PATENT DOCUMENTS

| | | |
|---|---|---|
| 2019/0148021 A1 | 5/2019 | Styner et al. |
| 2020/0357119 A1* | 11/2020 | Siemionow .............. G06N 3/08 |
| 2020/0381096 A1* | 12/2020 | Zaharchuk ........... G06K 9/6256 |
| 2021/0216826 A1* | 7/2021 | Hsieh ....................... G06N 5/04 |
| 2022/0039732 A1* | 2/2022 | Mahon ................... A61B 5/746 |

FOREIGN PATENT DOCUMENTS

| | | |
|---|---|---|
| CN | 109993210 | 7/2019 |
| CN | 110070935 | 7/2019 |
| CN | 110148142 | 8/2019 |
| CN | 110391014 | 10/2019 |
| WO | 2019086555 | 5/2019 |
| WO | 2019136745 | 7/2019 |

* cited by examiner

MODEL TRAINING METHOD AND ELECTRONIC DEVICE

CROSS-REFERENCE TO RELATED APPLICATION

This application claims the priority benefit of Taiwan application serial no. 109100915, filed on Jan. 10, 2020. The entirety of the above-mentioned patent application is hereby incorporated by reference herein and made a part of this specification.

BACKGROUND

Technical Field

The disclosure relates to a model training method and an electronic device, and in particular, to a model training method for a brain age prediction model and an electronic device.

Description of Related Art

Both mental illness and neurodegenerative diseases may accelerate brain degeneration of a patient (e.g., accelerate atrophy of the gray matter volume of brain). In the past, when determining a brain magnetic resonance image, a clinician makes his/her determination based on the medical and professional training that the clinician received. The clinician then performs clinical interpretation and provides a subjective diagnostic report according to his/her experience accumulated for a long period of time. Nevertheless, through such interpretation mechanism, different clinicians may provide different interpretation results as affected by their different experiences and backgrounds. Besides, such existing interpretation manner also fails to provide a quantitative indicator exhibiting high reproducibility for clearly and precisely portraying accelerated brain degeneration of a patient.

SUMMARY

The disclosure provides a model training method and an electronic device through which overall brain changes of an individual may be automatically and systematically evaluated, and a brain age of the individual may be predicted.

The disclosure provides a model training method for an electronic device, and the method includes the following steps. A brain age prediction model is established according to a training set. The training set includes a plurality of first human brain images identified as healthy. At least one parameter in the brain age prediction model is adjusted according to a validation set. The validation set includes a plurality of second human brain images identified as healthy. A plurality of third human brain images identified as unhealthy in a testing set are inputted into the brain age prediction model with the adjusted at least one parameter to obtain a plurality of first predicted brain ages corresponding to the plurality of third human brain images respectively. Whether the plurality of first predicted brain ages satisfy at least one first specific condition is determined. When the plurality of first predicted brain ages satisfy the at least one first specific condition, training of the brain age prediction model is completed.

The disclosure further provides an electronic device including an input circuit and a processor. The input circuit is configured to obtain a training set, a validation set, and a test set. The training set includes a plurality of first human brain images identified as healthy. The validation set includes a plurality of second human brain images identified as healthy, and the test set includes a plurality of third human brain images identified as unhealthy. The processor is coupled to the input circuit and configured to perform the following operations. A brain age prediction model is established according to the training set. At least one parameter in the brain age prediction model is adjusted according to the validation set. The plurality of third human brain images are inputted into the brain age prediction model with the adjusted at least one parameter to obtain a plurality of first predicted brain ages corresponding to the plurality of third human brain images respectively. Whether the plurality of first predicted brain ages satisfy at least one first specific condition is determined. When the plurality of first predicted brain ages satisfy the at least one first specific condition, training of the brain age prediction model is completed.

To sum up, the model training method and the electronic device provided by the embodiments of the disclosure are configured to perform automatic brain age prediction based on the whole brain structural covariance network. In the model training method and the electronic device provided by the disclosure, the features of the structural covariance network of the gray matter volume are extracted from the magnetic resonance images of brain. Besides, several machine learning algorithms are introduced. Overall brain changes of an individual are automatically and systematically evaluated, so that the brain age of the individual is predicted. The model generated through the model training method provided by the disclosure may be used to facilitate objective understanding of brain degeneration of the individual for clinical personnel, to further facilitate diagnosis of clinical diseases, and to act as a biological indicator.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

A model training method provided by the disclosure is suitable for an electronic device (not shown). The electronic device includes an input circuit (not shown). The input circuit is coupled to a processor. The input circuit is, for example, an input interface or a circuit configured to obtain related data outside the electronic device or from other sources.

The processor may be a central processing unit (CPU) or may be a programmable microprocessor for general or special use, a digital signal processor (DSP), a programmable controller, an application specific integrated circuit (ASIC), other similar elements, or a combination of the foregoing elements.

In addition, the electronic device may further include a storage circuit (not shown). The storage circuit may be a fixed or movable random access memory (RAM) of any form, a read-only memory (ROM), a flash memory, a similar element, or a combination of the foregoing elements.

In this embodiment, a plurality of program code snippets are stored in the storage device of the electronic device, and the program code snippets are executed by the processor after being installed. For instance, the storage circuit includes a plurality of modules, operations applied in the electronic device are executed through these modules, and each of the modules is formed by one or plural code snippets. Nevertheless, the disclosure is not limited thereto, and the operations of the electronic device may also be implemented through using other hardware forms.

Figure 1:
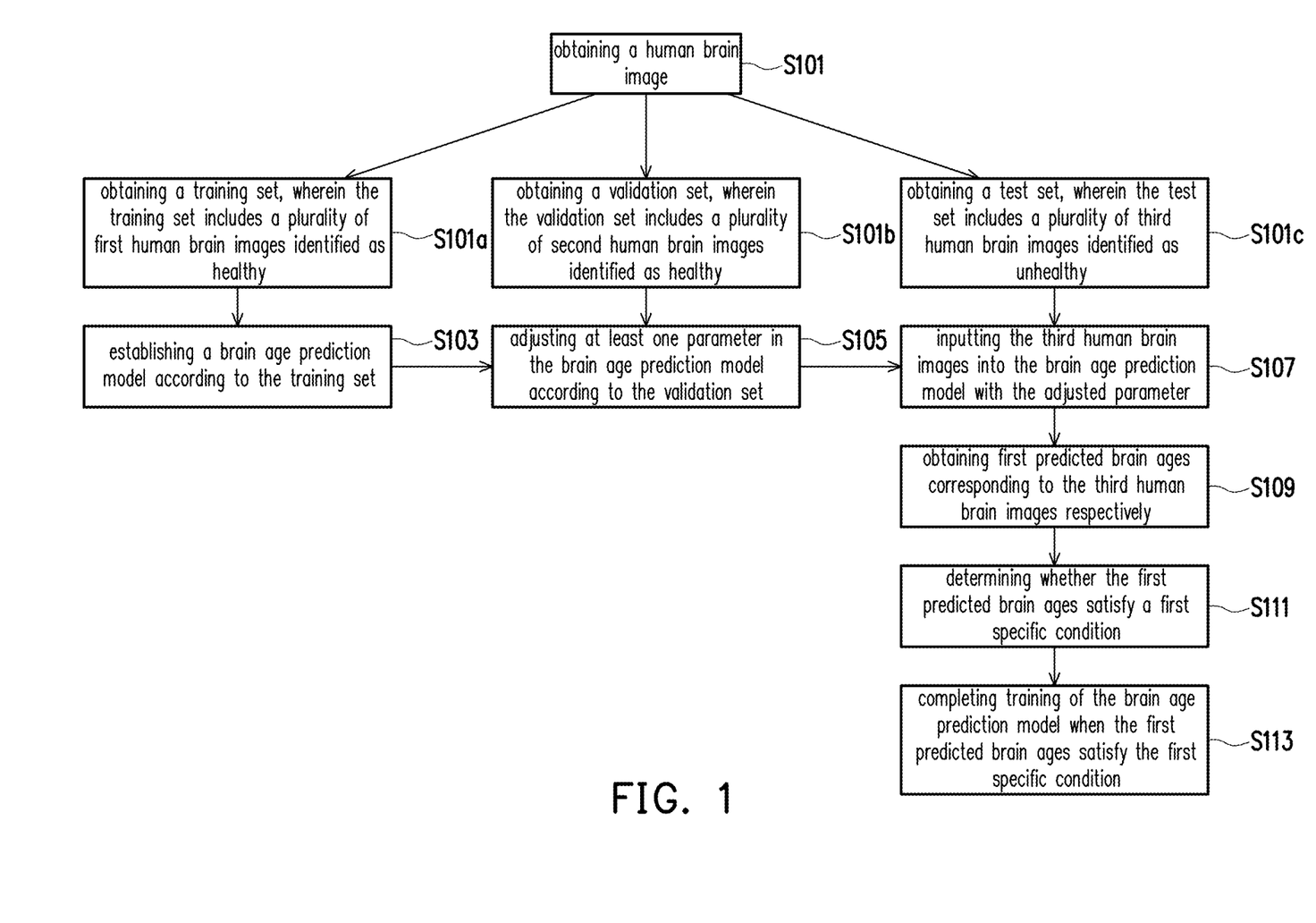
FIG. 1 is a schematic diagram of a model training method according to an embodiment of the disclosure.

FIG. 1 is a schematic diagram of a model training method according to an embodiment of the disclosure.

Referring to FIG. 1, in step S101, the input circuit may obtain a human brain image. The human brain image may be a T1-weighted image obtained through the magnetic resonance imaging (MRI) technique or may be a human brain image obtained through other techniques. In particular, step S101 may be further divided into step S101a to step S101c.

Specifically, in step S101a, the processor may obtain a training set, and such training set may include a plurality of human brain images (also called as first human brain images) identified as healthy. In this embodiment, a number of the first human brain images is eight hundred; nevertheless, the disclosure is not intended to limit the number of the first human brain images. Besides, the description of "human brain images identified as healthy" refers to, for example, human brain images of people not being diagnosed with (or determined to have) mental illness or neurodegenerative diseases by a doctor. Note that each of the first human brain images in the training set is marked with an actual age of a subject in the image, and a brain age of a healthy subject may be identical to (or close to) the actual age of the subject.

In step S101b, the processor may obtain a validation set, and such validation set may include a plurality of human brain images (also called as second human brain images) identified as healthy. In this embodiment, a number of the second human brain images is one hundred; nevertheless, the disclosure is not intended to limit the number of the second human brain images. Similarly, the description of "human brain images identified as healthy" refers to, for example, human brain images of people not being diagnosed with (or determined to have) mental illness or neurodegenerative diseases by a doctor. Note that each of the second human brain images in the validation set is marked with a brain age of a subject in the image, and the brain age of a healthy subject may be identical to (or close to) the actual age of the subject.

In step S101c, the processor may obtain a test set, and such test set may include a plurality of human brain images (also called as third human brain images) identified as unhealthy. In this embodiment, a number of the third human brain images is seventy-five; nevertheless, the disclosure is not intended to limit the number of the third human brain images. Besides, the description of "human brain images identified as unhealthy" refers to, for example, human brain images of people being diagnosed with (or determined to have) mental illness or neurodegenerative diseases by a doctor. Note that each of the third human brain images in the test set is marked with a brain age of a subject in the image. Note that the brain age of an unhealthy subject may be identified by a doctor, and the brain age of the subject identified as unhealthy is generally greater than (for example, greater than a threshold) the actual age of the subject.

When establishing a brain age prediction model, in step S103, the processor establishes the brain age prediction model according to the first human brain images in the training set. In particular, FIG. 2 is a detailed flow chart of step S103 according to an embodiment of the disclosure.

Figure 2:
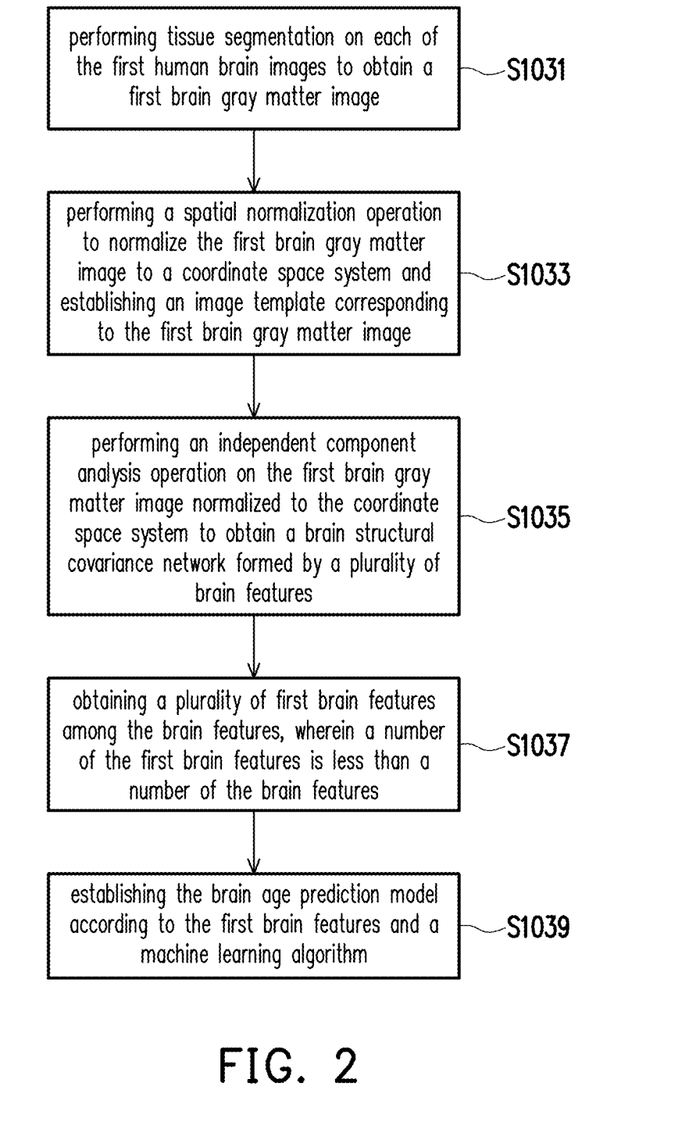
FIG. 2 is a detailed flow chart of step S103 according to an embodiment of the disclosure.

With reference to FIG. 2, step S103 may further include step S1031 to step S1039. After obtaining the plurality of first human brain images in the training set, in step S1031, the processor may perform tissue segmentation on each of the first human brain images to obtain a brain gray matter image (also called as a first brain gray matter image). In step S1033, the processor may perform a spatial normalization operation to normalize (or register) the first brain gray matter image to a coordinate space system and establish an image template corresponding to the first brain gray matter image. The coordinate space system is, for example, the Montreal Neurological Institute (MRI) space.

In step S1035, the processor may perform an independent component analysis operation on the first brain gray matter image normalized to the coordinate space system to obtain a brain structural covariance network formed by a plurality of brain features. Note that the brain features in the brain structural covariance network represent features of a common change (e.g., increasing or decreasing) in human brains of the plurality of first human brain images, and these features may be used to effectively predict the brain age.

In step S1037, the processor may obtain some features (also called as first brain features) among the plurality of brain features in the brain structural covariance network. In particular, a number of the first brain features may be less than a number of the plurality of brain features. Nevertheless, accuracy of predicting the brain age by using the first brain features is close to accuracy of predicting the brain age by using all of the brain features in the brain structural covariance network. For instance, a difference between the accuracy of predicting the brain age by using the first brain features and the accuracy of predicting the brain age by using all of the brain features in the brain structural covariance network is less than a threshold.

For instance, it is assumed that the brain structural covariance network includes one hundred and fifty features. The processor may calculate a mean absolute error (MAE) and a coefficient of determination (denoted $R^2$) of these one hundred and fifty features and finds a change trend of these one hundred and fifty features according to MAE and $R^2$. In particular, it is assumed that after a certain number of features (e.g., forty features), the change trend is no longer obvious, and in this case, the processor may select this number of features to act as the first brain features. Moreover, an ability of these first brain features to predict the brain age is close to an ability to predict the brain age by using all of the features in the brain structural covariance network. Besides, the features in the brain structural covariance network treated as the first brain features are obtained through repeated experiments, and description thereof is not provided herein.

Next, in step S1039, the processor establishes the brain age prediction model according to the first brain features and a machine learning algorithm. For instance, the processor may train the brain age prediction model according to the first brain features and the machine learning algorithm and uses a nested cross-validation technique to select hyperparameters related to the machine learning algorithm, so as to establish a brain age prediction model exhibiting a favorable deduction ability on the basis of the brain structural covariance network. The machine learning algorithm is an algorithm of, for example, lasso regression, elastic net regression, support vector regression, random forest regression, or XGBoost regression.

With reference to FIG. 1 again, after the brain age prediction model is established, in step S105, the processor may adjust at least one parameter (or weight) in the brain age prediction model according to the second human brain images in the validation set. In particular, FIG. 3 is a detailed flow chart of step S105 according to an embodiment of the disclosure.

Figure 3:
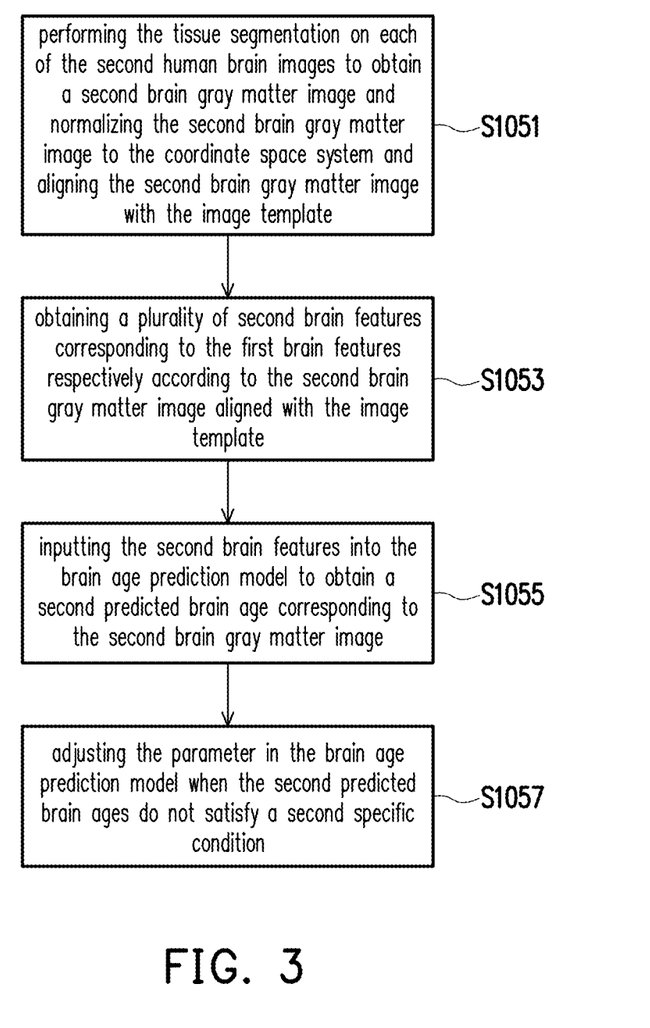
FIG. 3 is a detailed flow chart of step S105 according to an embodiment of the disclosure.

With reference to FIG. 3, step S105 may further include step S1051 to step S1057. In step S1051, the processor may perform the tissue segmentation on each of the second human brain images in the validation set to obtain a second brain gray matter image, and normalize the second brain gray matter image to the coordinate space system and align the second brain gray matter image with the previously-established image template. Alignment with the image template is to allow the human brain images of different sizes to be scaled to a same size for comparison.

Next, in step S1053, the processor obtains a plurality of features (also called as second brain features) corresponding to the plurality of first brain features respectively according to the second brain gray matter image aligned with the image template. Note that the second brain features and the first brain features are respectively features representing identical characteristics in different human brains.

In step S1055, the processor may then input the second brain features into the previously-established brain age prediction model to obtain a predicted brain age (also called as a second predicted brain age) corresponding to the second brain gray matter image. When the second predicted brain ages do not satisfy a specific condition (also called as a second specific condition), the processor may adjust the parameter in the brain age prediction model in step S1057. The second specific condition is to find out, for example, whether a difference between the second predicted brain ages and actual brain ages falls within a threshold. In particular, an estimation result of the second predicted brain ages may be used to facilitate understanding of an ability of the brain age prediction model to deduce the brain age of an unknown case. In this way, the deduction ability of the brain age prediction model may be stabilized without over fitting.

With reference to FIG. 1 again, after step S105 is performed, in step S107, the processor may input the third human brain images of the test set into the brain age prediction model with the adjusted parameter. In step S109, the processor may obtain predicted brain ages (also called as first predicted brain ages) corresponding to the third human brain images respectively. In particular, FIG. 4 is a detailed flow chart of step S109 according to an embodiment of the disclosure.

Figure 4:
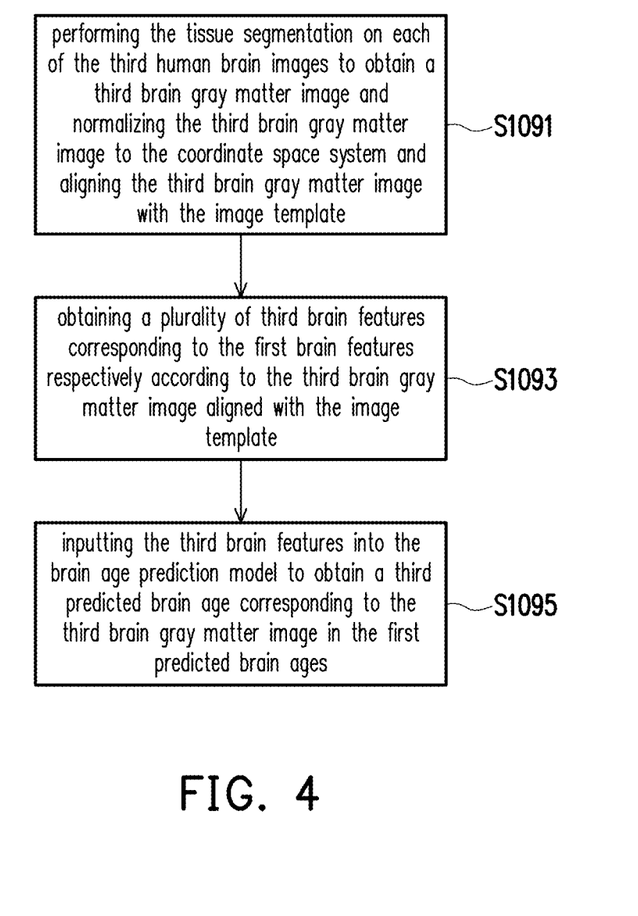
FIG. 4 is a detailed flow chart of step S109 according to an embodiment of the disclosure.

With reference to FIG. 4, step S109 may further include step S1091 to step S1095.

In step S1091, similar to the previous step S1051, the processor may perform the tissue segmentation on each of the third human brain images in the test set to obtain a brain gray matter image (also called as a third brain gray matter image) and normalize the third brain gray matter image to the coordinate space system and align the third brain gray matter image with the image template. Next, in step S1093, the processor obtains a plurality of brain features (also called as third brain features) corresponding to the plurality of first brain features respectively according to the third brain gray matter image aligned with the image template. Note that the third brain features and the first brain features are respectively features representing identical characteristics in different human brains. In the following step S1095, the processor may input the third brain features into the brain age prediction model to obtain a predicted brain age (also called as a third predicted brain age) corresponding to the third brain gray matter image in the plurality of first predicted brain ages.

With reference to FIG. 1 again, after step S109 is performed, in step S111, the processor may determine whether the first predicted brain ages satisfy a specific condition (also called as a first specific condition). The first specific condition is to find out, for example, whether a difference between the first predicted brain ages and the actual brain ages falls within a threshold. When the first predicted brain ages satisfy the first specific condition, in step S113, the processor may complete the training of the brain age prediction model. The trained brain age prediction model may then be used to predict brain ages.

Note that the brain age prediction model may also be generated by applying a deep learning network technique.

Figure 5:
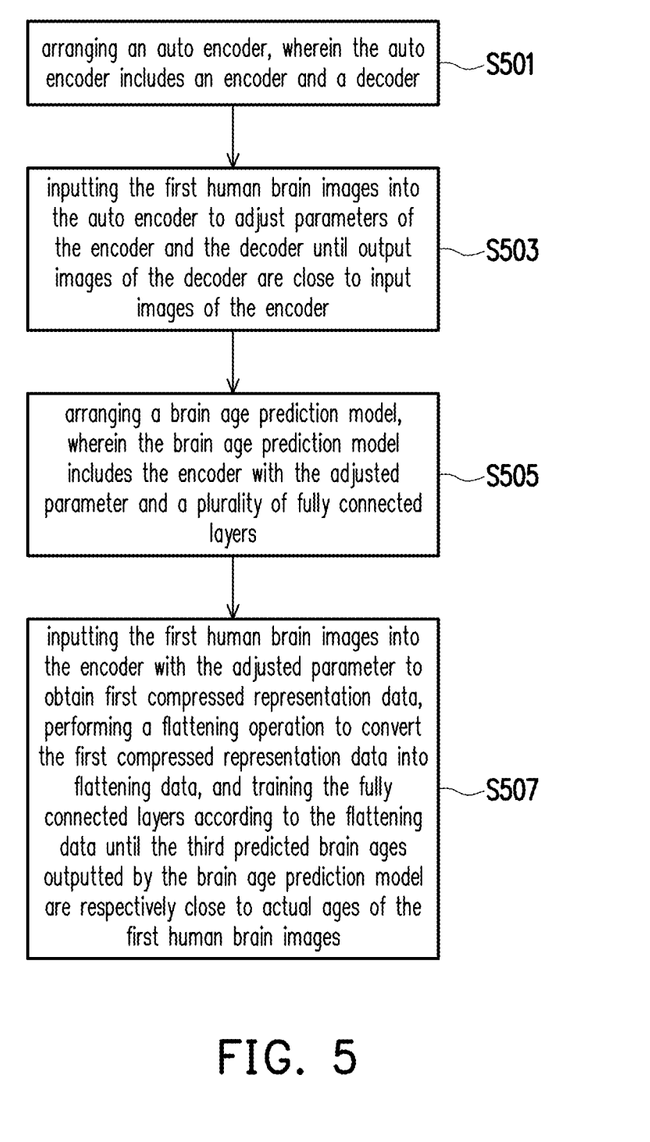
FIG. 5 is a flow chart of establishing a brain age prediction model by using a deep learning network according to an embodiment of the disclosure.
Figure 6:
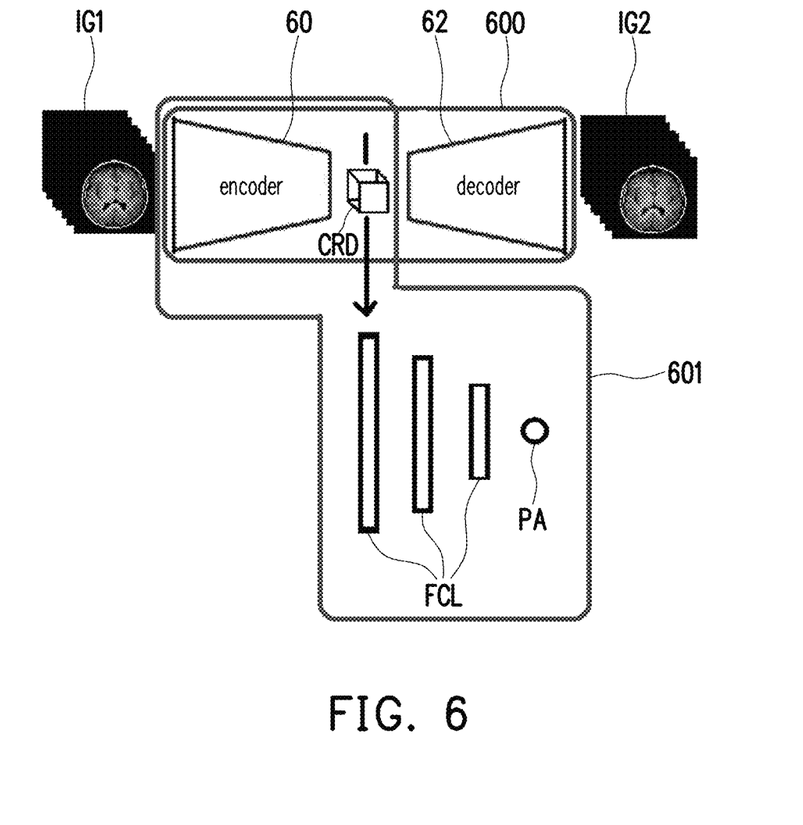
FIG. 6 is a schematic diagram of establishing the brain age prediction model by using the deep learning network according to an embodiment of the disclosure.

Specifically, FIG. 5 is a flow chart of establishing a brain age prediction model by using a deep learning network according to an embodiment of the disclosure. FIG. 6 is a schematic diagram of establishing the brain age prediction model by using the deep learning network according to an embodiment of the disclosure.

With reference to FIG. 5 and FIG. 6 together, first, in step S501, an auto encoder 600 is arranged in the processor, and the auto encoder 600 may include an encoder 60 and a decoder 62. Note that the main function of the auto encoder 600 is to obtain compressed representation data CRD after extracting features (or reduces dimensions) from input images IG1 (e.g., the first human brain images) through the encoder 60. The decoder 62 re-establishes output images IG2 according to the compressed representation data CRD, and the output images IG2 are significantly close to the input images IG1.

In step S503, the processor may input human brain images IG1 into the auto encoder 600 to adjust parameters of the encoder 60 and the decoder 62 until the output images IG2 of the decoder 62 are significantly close to the input images IG1 of the encoder 60, and in this way, the output images IG2 may be significantly close to the input images IG1. Herein, closeness of the two types of images is, for example, a difference (or a difference value) of the two types of images being less than a threshold.

In the following step S505, a brain age prediction model 601 is arranged in the processor. Here, the brain age prediction model 601 may include the encoder 60 with the adjusted parameter and a plurality of fully connected layers FCL. In step S507, the processor may input the human brain images IG1 (e.g., the first human brain images) into the encoder 60 with the adjusted parameter to obtain first compressed representation data, perform a flattening operation to convert the first compressed representation data into flattening data, and train the fully connected layers FCL according to the flattening data until a plurality of predicted brain ages PA (also called as the third predicted brain ages)

outputted by the brain age prediction model 601 are respectively close to actual ages of the human brain images IG1. Note that the flattening operation refers to, for example, configuring the compressed representation data to be arranged in a row, and data generated in this manner is called as the flattening data.

Next, the processor may adjust the parameter in the brain age prediction model 601 by using the validation set. For instance, the processor may adjust weights of the fully connected layers FCL in the brain age prediction model 601 according to the plurality of second human brain images in the validation set until a plurality of predicted brain ages (also called as fourth predicted brain ages) outputted by the brain age prediction model 601 are close to the actual ages of the plurality of second human brain images respectively. Note that in such a manner, the processor may adjust the weights of the fully connected layers FCL until a minimum difference between the plurality of predicted brain ages (also called as the fourth predicted brain ages) outputted by the brain age prediction model 601 and the actual ages of the plurality of second human brain images is provided. In this way, training of the brain age prediction model 601 established by the deep learning technique is completed.

In view of the foregoing, the model training method and the electronic device provided by the embodiments of the disclosure are configured to perform automatic brain age prediction based on the whole brain structural covariance network. In the model training method and the electronic device provided by the disclosure, the features of the structural covariance network of the gray matter volume are extracted from the magnetic resonance images of brain. Besides, several machine learning algorithms are introduced. Overall brain changes of an individual are automatically and systematically evaluated, so that the brain age of the individual is predicted. The model generated through the model training method provided by the disclosure may be used to facilitate objective understanding of brain degeneration of the individual for clinical personnel, to further facilitate diagnosis of clinical diseases, and to act as a biological indicator.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A model training method for an electronic device, the method comprising:
    establishing a brain age prediction model according to a training set, wherein the training set comprises a plurality of first human brain images identified as healthy, wherein the step of establishing the brain age prediction model according to the training set further comprises:
        arranging an auto encoder, wherein the auto encoder comprises an encoder and a decoder;
        inputting the plurality of first human brain images into the auto encoder to adjust parameters of the encoder and the decoder until output whether a difference between images of the decoder and input images of the encoder are located within an image predetermined value;
        arranging the brain age prediction model, wherein the brain age prediction model comprises the encoder with the adjusted parameter and a plurality of fully connected layers; and
        inputting the plurality of first human brain images into the encoder with the adjusted parameter to obtain first compressed representation data and training the plurality of fully connected layers according to the first compressed representation data until whether a difference between the plurality of third predicted brain ages outputted by the brain age prediction model and actual ages of the plurality of first human brain images are located within the predetermined value respectively;
    adjusting at least one parameter in the brain age prediction model according to a validation set, wherein the validation set comprises a plurality of second human brain images identified as healthy;
    inputting a plurality of third human brain images identified as unhealthy in a testing set into the brain age prediction model with the adjusted at least one parameter to obtain a plurality of first predicted brain ages corresponding to the plurality of third human brain images respectively;
    determining whether the plurality of first predicted brain ages satisfy at least one first specific condition; and
    completing training of the brain age prediction model when the plurality of first predicted brain ages satisfy the at least one first specific condition, wherein the at least one first specific condition comprises whether a difference between the first predicted brain ages and actual brain ages are located within a predetermined value.

2. The model training method as claimed in claim 1, wherein the step of establishing the brain age prediction model according to the training set further comprises:
    performing tissue segmentation on each of the plurality of first human brain images to obtain a first brain gray matter image;
    normalizing the first brain gray matter image to a coordinate space system and establishing an image template corresponding to the first brain gray matter image;
    obtaining a plurality of first brain features among a plurality of brain features according to the first brain gray matter image normalized to the coordinate space system, wherein a number of the plurality of first brain features is less than a number of the plurality of brain features; and
    establishing the brain age prediction model according to the plurality of first brain features and a machine learning algorithm.

3. The model training method as claimed in claim 2, wherein the step of normalizing the first brain gray matter image to the coordinate space system further comprises:
    performing a spatial normalization operation to normalize the first brain gray matter image to the coordinate space system.

4. The model training method as claimed in claim 2, wherein the step of obtaining the plurality of first brain features among the plurality of brain features according to the first brain gray matter image normalized to the coordinate space system further comprises:
    performing an independent component analysis operation on the first brain gray matter image normalized to the coordinate space system to obtain a brain structural covariance network formed by the plurality of brain features; and
    obtaining the plurality of first brain features in the brain structural covariance network, wherein a difference between accuracy of predicting a brain age by using the plurality of first brain features between accuracy of predicting the brain age by using the plurality of brain features are located within an accuracy predetermined value.

5. The model training method as claimed in claim 2, wherein the step of adjusting the at least one parameter in the brain age prediction model according to the validation set further comprises:
performing the tissue segmentation on each of the plurality of second human brain images to obtain a second brain gray matter image;
normalizing the second brain gray matter image to the coordinate space system and aligning the second brain gray matter image with the image template;
obtaining a plurality of second brain features corresponding to the plurality of first brain features respectively according to the second brain gray matter image aligned with the image template;
inputting the plurality of second brain features into the brain age prediction model to obtain a second predicted brain age corresponding to the second brain gray matter image; and
performing the step of adjusting the at least one parameter in the brain age prediction model when the plurality of second predicted brain ages do not satisfy a second specific condition, wherein the second specific condition comprises whether a difference between the second predicted brain ages and actual brain ages are located within the predetermined value.

6. The model training method as claimed in claim 2, wherein the step of inputting the plurality of third human brain images identified as unhealthy into the brain age prediction model with the adjusted at least one parameter to obtain the plurality of first predicted brain ages corresponding to the plurality of third human brain images respectively further comprises:
performing the tissue segmentation on each of the plurality of third human brain images to obtain a third brain gray matter image;
normalizing the third brain gray matter image to the coordinate space system and aligning the third brain gray matter image with the image template;
obtaining a plurality of third brain features corresponding to the plurality of first brain features respectively according to the third brain gray matter image aligned with the image template; and
inputting the plurality of third brain features into the brain age prediction model to obtain a third predicted brain age corresponding to the third brain gray matter image in the plurality of first predicted brain ages.

7. The model training method as claimed in claim 1, wherein the step of adjusting the at least one parameter in the brain age prediction model according to the validation set further comprises:
adjusting weights of the plurality of fully connected layers in the brain age prediction model according to the plurality of second human brain images until whether a difference between a plurality of fourth predicted brain ages outputted by the brain age prediction model and actual ages of the plurality of second human brain images are located within the predetermined value respectively.

8. The model training method as claimed in claim 1, wherein the step of training the plurality of fully connected layers according to the first compressed representation data further comprises:
performing a flattening operation to convert the first compressed representation data into flattening data; and
training the plurality of fully connected layers according to the flattening data.

9. An electronic device, comprising:
an input circuit, configured to obtain a training set, a validation set, and a test set, wherein the training set comprises a plurality of first human brain images identified as healthy, the validation set comprises a plurality of second human brain images identified as healthy, and the test set comprises a plurality of third human brain images identified as unhealthy; and
a processor, coupled to the input circuit and configured to perform the following operations:
establishing a brain age prediction model according to the training set, wherein the operation of establishing the brain age prediction model according to the training set further comprises:
arranging an auto encoder, wherein the auto encoder comprises an encoder and a decoder;
inputting the plurality of first human brain images into the auto encoder to adjust parameters of the encoder and the decoder until output whether a difference between images of the decoder and input images of the encoder are located within an image predetermined value;
arranging the brain age prediction model, wherein the brain age prediction model comprises the encoder with the adjusted parameter and a plurality of fully connected layers; and
inputting the plurality of first human brain images into the encoder with the adjusted parameter to obtain first compressed representation data and training the plurality of fully connected layers according to the first compressed representation data until whether a difference between the plurality of third predicted brain ages outputted by the brain age prediction model and actual ages of the plurality of first human brain images are located within the predetermined value respectively;
adjusting at least one parameter in the brain age prediction model according to the validation set;
inputting the plurality of third human brain images into the brain age prediction model with the adjusted at least one parameter to obtain a plurality of first predicted brain ages corresponding to the plurality of third human brain images respectively;
determining whether the plurality of first predicted brain ages satisfy at least one first specific condition; and
completing training of the brain age prediction model when the plurality of first predicted brain ages satisfy the at least one first specific condition, wherein the at least one first specific condition comprises whether a difference between the first predicted brain ages and actual brain ages are located within a predetermined value.

* * * * *